United States Patent [19]
Morgenstern et al.

[11] Patent Number: 6,005,140
[45] Date of Patent: *Dec. 21, 1999

[54] PROCESS FOR MAKING GLYPHOSATE BY OXIDIZING N-SUBSTITUTED GLYPHOSATES

[75] Inventors: David A. Morgenstern, Creve Coeur; Yvette M. Fobian, Labadie, both of Mo.

[73] Assignee: Monsanto Company, St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 09/023,404

[22] Filed: Feb. 12, 1998

[30] Foreign Application Priority Data

Feb. 12, 1998 [WO] WIPO .................. PCTUS9802883

[51] Int. Cl.$^6$ .................. C07F 9/38; C07F 9/40
[52] U.S. Cl. .................. 562/17; 558/145; 558/155; 558/169; 560/155; 562/12
[58] Field of Search .................. 558/145; 562/12, 562/17

[56] References Cited

U.S. PATENT DOCUMENTS

| | | | |
|---|---|---|---|
| 3,583,972 | 6/1971 | Birkenmeyer et al. | 260/210 R |
| 3,799,758 | 3/1974 | Franz et al. | 71/86 |
| 3,835,000 | 9/1974 | Frazier et al. | 204/78 |
| 3,927,080 | 12/1975 | Gaertner | 260/502.5 |
| 3,950,402 | 4/1976 | Franz | 260/502.5 |
| 3,954,848 | 5/1976 | Franz | 260/502.5 |
| 3,956,370 | 5/1976 | Parry et al. | 260/502.5 |
| 3,969,398 | 7/1976 | Hershman | 260/502.5 |
| 4,026,950 | 5/1977 | Le Ludec . | |
| 4,147,719 | 4/1979 | Franz | 260/501.12 |
| 4,264,776 | 4/1981 | Hershman et al. | 564/384 |
| 4,507,250 | 3/1985 | Bakel | 260/502.5 |
| 4,525,294 | 6/1985 | Sartori et al. | 252/182 |
| 4,582,650 | 4/1986 | Felthouse . | |
| 4,654,429 | 3/1987 | Balthazor et al. | 558/145 |
| 4,775,498 | 10/1988 | Gentilcore | 260/502.5 |
| 4,810,426 | 3/1989 | Fields, Jr. et al. | 260/502.5 |
| 4,851,131 | 7/1989 | Grabiak et al. . | |
| 4,921,991 | 5/1990 | Lacroix | 558/169 X |
| 4,978,649 | 12/1990 | Surovikin et al. | 502/416 |
| 5,068,404 | 11/1991 | Miller et al. | 502/17 |
| 5,179,228 | 1/1993 | Ramon et al. | 562/17 |
| 5,292,936 | 3/1994 | Franczyk | 562/526 |
| 5,367,112 | 11/1994 | Franczyk | 562/526 |
| 5,500,485 | 3/1996 | Hodgkinson | 562/18 |
| 5,602,276 | 2/1997 | Stern et al. | 562/16 |
| 5,606,107 | 2/1997 | Smith | 562/17 |
| 5,627,125 | 5/1997 | Ebner et al. | 502/331 |
| 5,703,273 | 12/1997 | Stern et al. | 562/16 |

FOREIGN PATENT DOCUMENTS

| | | | |
|---|---|---|---|
| 0055695 | 7/1982 | European Pat. Off. | C07F 9/38 |
| 0 680 948 A1 | 4/1995 | European Pat. Off. . | |
| 8-333310 | 12/1996 | Japan . | |

OTHER PUBLICATIONS

F. Coloma et al., "Preparation Of Platinum Supported On Pregraphitized Carbon Blacks", *Langmuir*, vol. 10, pp. 750–755, 1994.

F. Coloma et al., "Heat–Treated Carbon Blacks As Supports For Platinum Catalysts", *Journal of Catalysis*, vol. 154, pp. 299–305, 1995.

Mallat et al., "Preparation Of Promoted Platinum Catalysts Of Designed Geometry And The Role Of Promoters In The Liquid–Phase Oxidation Of 1–Methoxy–2–Propanol", *Journal of Catalysis*, vol. 142, pp. 237–253, 1993.

Kyong Tae Kim et al., "Preparation Of Carbon–Supported Platinum Catalysts: Adsorption Mechanism Of Anionic Platinum Precursor Onto Carbon Support", *Carbon*, vol. 30, No. 3, pp. 467–475, 1992.

F. Rodriguez–Reinoso et al., "Platinum Catalysts Supported On Activited Carbons", *Journal of Catalysis*, vol. 99, pp. 171–183, 1986.

H.E. Van Dam et al., "Preparation Of Platinum On Activated Carbon", *Journal of Catalysis*, vol. 131, pp. 335–349, 1991.

A. Cope et al. "Synthesis of 2–Alkylaminoethanols from Ethanolamine" Journal of American Chemistry Society, vol. 64 (Jul. 1942) pp. 1503–1506.

(List continued on next page.)

*Primary Examiner*—Michael G. Ambrose
*Attorney, Agent, or Firm*—Senniger, Powers, Leavitt & Roedel

[57] ABSTRACT

This invention is directed to process for making a composition having the formula (I):

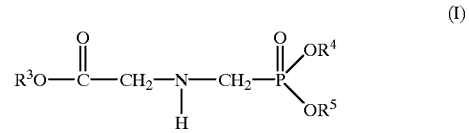

wherein $R^3$, $R^4$, and $R^5$ are independently hydrogen, substituted or unsubstituted hydrocarbyl, or an agronomically acceptable cation. The process comprises contacting a solution with a noble metal catalyst and introducing oxygen into the solution. The solution contains an N-substituted glyphosate having the formula (II):

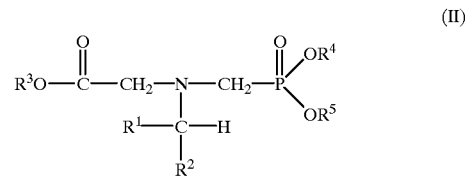

wherein $R^1$ and $R^2$ are independently hydrogen, halogen, $-PO_3H_2$, $-SO_3H$, $-NO_2$, or substituted or unsubstituted hydrocarbyl other than $-CO_2H$. $R^3$, $R^4$, and $R^5$ are as defined for formula (I).

This invention also relates to an oxidation catalyst comprising a noble metal having a hydrophobic electroactive molecular species adsorbed thereon.

50 Claims, 2 Drawing Sheets

OTHER PUBLICATIONS

S. Dapperheld et al. "Organic Electron Transfer Systems. II. Substituted Triarylamine Cation–Radical Redox Systems–Synthesis, Electrochemical and Spectroscopic Properties. Hammet Behavior, and Suitaqbility as Redox Catalysts" Chem. Ber., vol. 124, No. 11 (1991) pp. 2557–2567. (Abstract Only).

G. Davis et al. "Oxidations of Amines VI. POlatinum–Catalyzed Air Oxidating of N–Methyl Tertiary Amines" Tetrahedron Letters, vol. 38 (1968) pp. 4085–4086.

D. Dolphin et al. "Polyhaloporphyrins: Unusual Ligands for Metals and Metal–Catalyzed Oxidations" Acc. Chem. Res., vol. 30, No. 6 (1997) pp. 251–259.

G. Dyker et al. "Amino Acid Derivatives by Multicomponent Reactions" Angew. Chem. Int. Ed. Engl., vol. 36, No. 16 (1997) pp. 1700–1702.

J. Franz et al. "Methods of Preparing Glyphosate" Glyphosate: A Unique Global Herbicide, Chapter 8, (1997) American Chemical Society, Washington, D.C., pp. 233–262.

J. Fuhrhop et al. "Reversible Reactions of Porphyrins and Metalloporphyrins and Electrochemistry", Porphyrins and Metalloporphyrins, Chapter 14, (1975) Elsevier Scientific Publishing Company, Amsterdam, The Netherlands, pp. 593–623.

J. Knifton "Amidocarbonylation" Applied Homogeneous Catalysis with Organometallic Compounds, vol. 1, Weinheim (1996) Germany, pp. 159–168.

L. Maier "Organic Phosphorus Compounds 95. A Simple Method for the Preparation of N–Dihydroxyphosphonylmethyl–Glycine (Glyphosate)" Phosphorous, Sulfur, and Silicon, vol. 61 (1991) pp. 65–67.

P. Mastalerz "α–Substituted Phosphonates" Handbook of Organophosphorus Chemistry, Robert Engel ed., Marcel Dekker (1992) pp. 277–371.

M. Masui et al. "N–Hydroxyphthalimide as an Effective Mediator for the Oxidation of Alcohols by Electrolysis" J. Chem. Soc., Chem. Communication (1983) pp. 479–480.

R. Moss "Preparation and Characterization of Supported Metal Catalysts" Experimetnal Methods in Catalytic Research, vol. II, Chapter 2 (1976) Academic Press, New York, pp. 43–94.

J. Perichon et al. "Miscellaneous Hydrocarbons" Encyclopedia of Electrochemistry of the Elements, vol. XI (1978) Marcel Dekker, Inc., New York, pp. 163–166.

D. Redmore "The Chemistry of P–C–N–Systems" Topics in Phosphorus Chemistry, vol. 8 (1976) John Wiley & Sons, pp. 515–585.

D. Riley et al. "Homogeneous Catalysts for Selective Molecular Oxygen Driven Oxidative Decarboxylations" J. Am. Chem. Soc., vol. 113, No. 9 (1991) pp. 3371–3378.

D. Riley et al. "Vanadium (IV,V) Salts as Homogeneous Catalysts for the Oxygen Oxidation of N–(Phosphonomethyl)iminodiacetic Acid to N–(Phosphonomethyl)glycine" Inorg. Chem., vol. 30, No. 22 (1991) pp. 4191–4197.

M. Semmelhack et al. "Nitroxyl–Mediated electrooxidation of Alcohols to Aldehydes and Ketones" J. Am. Chem. Soc., vol. 105, No. 13 (1983) pp. 4492–4494.

A. Stiles "Getting the Catalyst and the Support Together" Catalyst Supports and Supported Catalysts; Theoretical and Applied Concepts, Chapter 1 (1987) Butterworths, Boston, MA, pp. 1–137.

S. Torii et al. "Carboxylic Acids" Organic Electrochemistry, Chapter 14 (1991) Marcel Dekker, Inc., 3rd ed., New York, pp. 535–579.

PROCESS FOR MAKING GLYPHOSATE BY OXIDIZING N-SUBSTITUTED GLYPHOSATES

BACKGROUND OF THE INVENTION

This invention generally relates to a process for converting N-substituted N-(phosphonomethyl)glycines (sometimes referred to as "N-substituted glyphosate"), as well as esters and salts thereof, to N-(phosphonomethyl) glycine (sometimes referred to as "glyphosate"), as well as esters and salts thereof, via a noble-metal catalyzed oxidation reaction. This invention is particularly directed to converting N-substituted glyphosates, as well as esters and salts thereof, having a single N-carboxymethyl functionality.

Glyphosate is described by Franz in U.S. Pat. No. 3,799,758 and has the following formula:

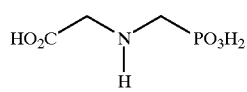

Glyphosate and its salts conveniently are applied as a post-emergent herbicide in an aqueous formulation. It is a highly effective and commercially important broad-spectrum herbicide useful in controlling the growth of germinating seeds, emerging seedlings, maturing and established woody and herbaceous vegetation, and aquatic plants.

Various methods for making glyphosate from N-substituted glyphosates are known in the art. For example, in U.S. Pat. No. 3,956,370, Parry et al. teach that N-benzylglycine may be phosphonomethylated to N-benzyl glyphosate, and then reacted with hydrobromic or hydroiodic acid to cleave the benzyl group and thereby produce glyphosate. In U.S. Pat. No. 3,927,080, Gaertner teaches that N-t-butylglycine may be phosphonomethylated to form N-t-butyl glyphosate, and then converted to glyphosate via acid hydrolysis. Glyphosate also may be produced from N-benzyl glyphosate via hydrogenolysis, as described, for example, in European Patent Application No. 55,695 and Maier, L. *Phosphorus, Sulfur and Silicon*, 61, 65–7 (1991). These processes are problematic in that they produce undesirable byproducts such as isobutylene and toluene which create difficulties due to their potential toxicities. Moreover, acid hydrolysis and hydrogenation of N-substituted glyphosates has been demonstrated only for alkyl groups such as tertiary butyl and benzyl groups which are known to be susceptible to such reactions. Dealkylation of N-methyl, N-isopropyl, and other N-substituted glyphosates which are not readily susceptible to acid hydrolysis or catalytic hydrogenation has not been demonstrated.

Other methods for making glyphosate are directed to oxidatively cleaving N-(phosphonomethyl)iminodiacetic acid (sometimes referred to as "PMIDA"):

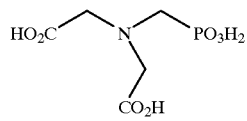

PMIDA may be synthesized from phosphorus trichloride, formaldehyde, and an aqueous solution of the disodium salt of iminodiacetic acid, as described by Gentilcore in U.S. Pat. No. 4,775,498:

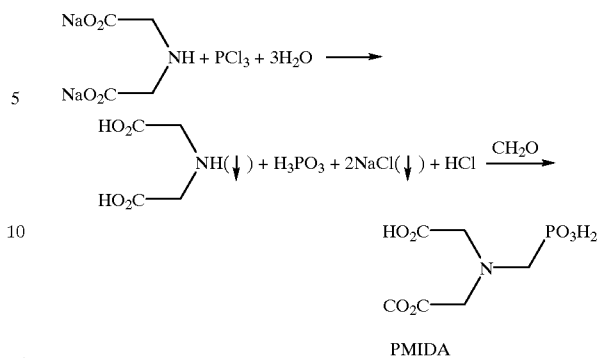

It is well-known in the art that PMIDA may be converted into glyphosate by heterogeneous oxidation over carbon catalysts as described, for example, in U.S. Pat. No. 3,950,402 to Franz and U.S. Pat. No. 4,654,429 to Balthazor et al.; by homogenous catalytic oxidation as described, for example, in Riley et al. *J. Amer. Chem. Soc.* 113, 3371–78 (1991) and Riley et al. *Inorg. Chem.* 30, 4191–97 (1991); and by electrochemical oxidation using carbon electrodes as described, for example, in U.S. Pat. No. 3,835,000 to Frazier et al. These oxidation methods, however, have been reported to be useful only for preparing glyphosate from PMIDA, an N-substituted glyphosate having two N-carboxymethyl functionalities. None of these prior art oxidation methods have been reported to be useful for preparing glyphosate from N-substituted glyphosate compounds having only one N-carboxymethyl functionality, i.e., where R' in the following formula is other than —CH$_2$CO$_2$H:

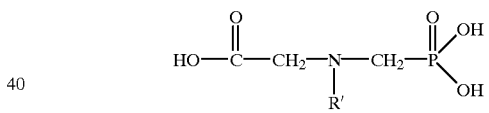

To the contrary, many prior art references suggest that if R' is a functionality other than a —CH$_2$CO$_2$H group, the prior art methods will cleave the —CH$_2$CO$_2$H group rather than R', and will therefore fail to produce glyphosate. This is particularly true for the prior art which is directed to heterogenous catalytic oxidations over carbon and electrochemical oxidations using carbon electrodes. The mechanisms for these oxidations are well known in the art, particularly for electrochemical oxidations where it is known as the Kolbe reaction, described in various organic electrochemistry books, e.g., S. Torii and H. Tanaka, *Organic Electrochemistry* 535–80 (H. Lund and M. M. Baizer eds., Marcel Dekker, 3rd ed. 1991). Both mechanisms involve the oxidative degradation of carboxylic acid to a carbon radical and carbon dioxide:

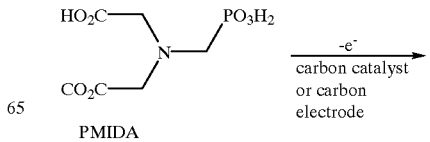

-continued

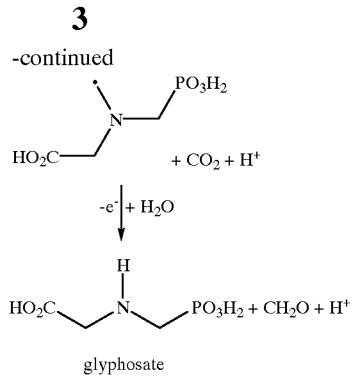

glyphosate

There is no suggestion that these mechanisms could be used to cleave any other functionality besides —CH$_2$CO$_2$H.

Thus, a more general method for oxidizing N-substituted glyphosates to glyphosates is therefore desirable. Such a method would allow a wider range of N-substituted glycines to be used as raw materials for the production of glyphosate. Such a method also could be used to make glyphosate from N-methylglyphosate (sometimes referred to as "NMG"), an undesirable byproduct from the carbon-catalyzed oxidation of PMIDA.

SUMMARY OF THE INVENTION

Among the objects of the invention, therefore, is to provide a process for making glyphosate (as well as its salts and esters) by oxidizing N-substituted glyphosates (as well as salts and esters thereof). More particularly, it is an object of this invention to provide a process for making glyphosate (as well as its salts and esters) by oxidizing N-substituted glyphosates (as well as salts and esters thereof) having a single N-carboxymethyl functionality. For example, it is an object of this invention to provide a process for making glyphosate by oxidizing NMG.

Briefly, therefore, the present invention is directed to a novel process for making a composition having the formula (I):

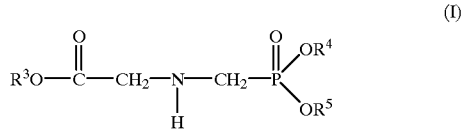

In this formula, $R^3$, $R^4$, and $R^5$ are independently hydrogen, substituted or unsubstituted hydrocarbyl, or an agronomically acceptable cation. This invention comprises contacting a solution with a noble metal catalyst and introducing oxygen into the solution. The solution contains an N-substituted glyphosate having the formula (II):

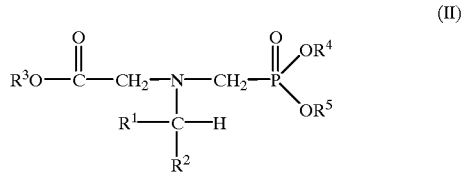

In formula (II), $R^1$ and $R^2$ are independently hydrogen, halogen, —PO$_3$H$_2$, —SO$_3$H, —NO$_2$, or substituted or unsubstituted hydrocarbyl other than —CO$_2$H. $R^3$, $R^4$, and $R^5$ are as defined above for formula (I) above.

In another embodiment of this invention, the composition (i.e., formula (I)) to be prepared is glyphosate or a salt thereof, and the N-substituted glyphosate (i.e., formula (II)) is NMG or a salt thereof. During the process, a solution having a temperature of from about 125 to about 150° C. and containing NMG or a salt thereof is contacted with a noble metal catalyst comprising platinum. Also during the process, 2,2,6,6-tetramethyl piperidine N-oxide is added to the solution. Further, oxygen is introduced into the solution at a rate which imparts a finite dissolved oxygen concentration in the solution that is no greater than 2.0 ppm.

A third embodiment of this invention is directed to a noble metal oxidation catalyst having a hydrophobic electroactive molecular species adsorbed on it.

DETAILED DESCRIPTION OF THE PREFERRED EMBODIMENTS

Figure 1:
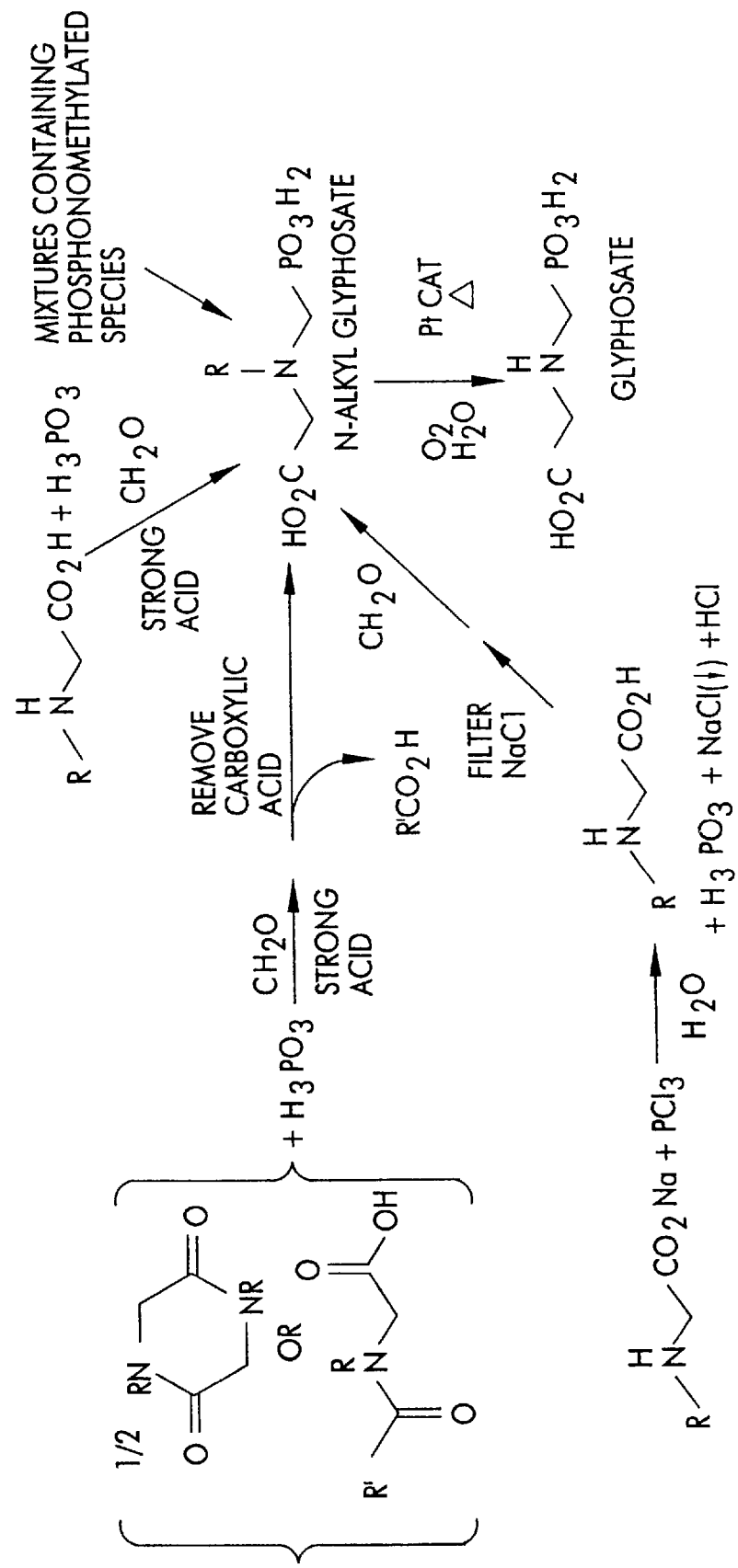
FIG. 1 shows the chemical steps that may be taken to produce glyphosate in accordance with this invention using various N-substituted glycine precursors.

The present invention provides a novel and useful method for manufacturing glyphosate, its salts, and its esters, in an aqueous medium wherein an N-substituted glyphosate or a salt or ester thereof (collectively referred to as "N-substituted glyphosate reactant") is oxidatively cleaved with oxygen over a noble metal catalyst. Advantages of preparing glyphosate from N-substituted glyphosates using this method include the simplicity of the procedure, the low cost of the oxidant (e.g., air or molecular oxygen), and the durability of the catalyst (i.e., little or no deactivation of the catalyst over several cycles).

Unlike the prior art methods for oxidatively cleaving N-substituted glyphosates to make glyphosate, this method is not limited to the oxidation of PMIDA (which has two N-carboxymethyl functionalities). Instead, this method also may be used to make glyphosate by oxidatively cleaving N-substituted glyphosates having only one N-carboxymethyl functionality. This invention, therefore, significantly widens the range of N-substituted glyphosates that may be oxidized to make glyphosate. This, in turn, significantly widens the range of N-substituted glycines (a precursor to many N-substituted glyphosates) which may serve as the raw material to prepare glyphosate. This invention also is valuable because it provides a method to prepare glyphosate from NMG, an undesirable byproduct from the carbon-catalyzed oxidation of PMIDA.

The N-substituted glyphosate reactants of the present invention have the following formula:

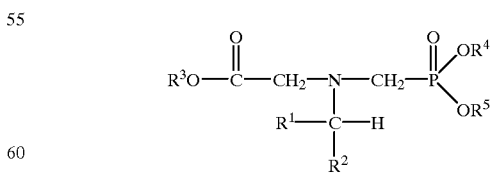

wherein preferably $R^1$ and $R^2$ are independently hydrogen, halogen, —PO$_3$H$_2$, —SO$_3$H, —NO$_2$, or a substituted or unsubstituted hydrocarbyl other than —CO$_2$H; and $R^3$, $R^4$, and $R^5$ are independently hydrogen, a substituted or unsubstituted hydrocarbyl, or an agronomically acceptable cation.

As used herein, the term "hydrocarbyl", is defined as a radical consisting exclusively of carbon and hydrogen. The hydrocarbyl may be branched or unbranched, may be saturated or unsaturated, and may contain one or more rings. Suitable hydrocarbyl moieties include alkyl, alkenyl, alkynyl, and aryl moieties. They also include alkyl, alkenyl, alkynyl, and aryl moieties substituted with other aliphatic or cyclic hydrocarbyl groups, such as alkaryl, alkenaryl and alkynaryl.

The term "substituted hydrocarbyl" is defined as a hydrocarbyl wherein at least one hydrogen atom has been substituted with an atom other than hydrogen. For example, the hydrogen atom may be replaced by a halogen atom, such as a chlorine or fluorine atom. The hydrogen atom alternatively may be substituted by an oxygen atom to form, for example, a hydroxy group, an ether, an ester, an anhydride, an aldehyde, a ketone, or a carboxylic acid (except that neither $R^1$ nor $R^2$ may be a carboxy group, i.e., $-CO_2H$). The hydrogen atom also may be replaced by a nitrogen atom to form an amide or a nitro functionality, although substitution by nitrogen to form an amine or a nitrile functionality preferably should be avoided. In addition, the hydrogen atom may be replaced with a sulfur atom to form, for example, $-SO_3H$, although substitution by sulfur to form a thiol should be avoided.

It should be recognized that $R^1$ and $R^2$ may together form a ring. This ring may be either a hydrocarbon ring or a heterocycle, and at least one hydrogen on the ring may be substituted as described above for substituted hydrocarbyl functionalities.

In a preferred embodiment, $R^1$, $R^3$, $R^4$, and $R^5$ are each hydrogen, and $R^2$ is a linear, branched, or cyclic hydrocarbyl containing up to about 19 carbon atoms. In a more preferred embodiment, $R^3$, $R^4$, and $R^5$ are each hydrogen, and $-CHR^1R^2$ is methyl (i.e., $R^1$ and $R^2$ are hydrogen), iso-propyl (i.e., $R^1$ and $R^2$ are $-CH_3$), benzyl (i.e., $R^1$ is hydrogen and $R^2$ is phenyl), or n-pentyl (i.e., $R^1$ is hydrogen and $R^2$ is a 4-carbon, straight-chain hydrocarbyl).

Many N-substituted glyphosate reactants may be prepared by phosphonomethylating the corresponding N-substituted glycines, their salts, or their amides, for example, by the following reaction:

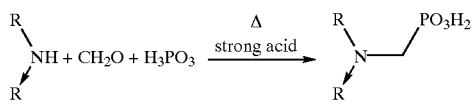

Phosphonomethylation of secondary amines is well-known in the art, and discussed at length in Redmore, D. *Topics in Phosphorous Chemistry*, Vol. 8, 515–85 (E. G. Griffith & M. Grayson eds., John Wiley & Sons 1976); and in a chapter entitled "α-substituted Phosphonates" in Mastalerz, P. *Handbook of Organophosphorus Chemistry* 277–375 (Robert Engel ed., Marcel Dekker 1992).

Several methods may be used to prepare N-substituted glycines and their salts and amides. In one embodiment of this invention, the N-substituted glycine is prepared by the condensation of hydrogen cyanide, formaldehyde, and N-substituted amines, followed by hydrolysis to N-substituted glycine or a salt thereof:

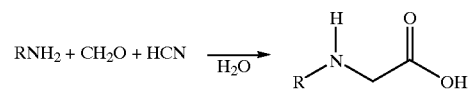

This reaction is known as the Strecker synthesis. The Strecker synthesis is well-known in the art and is described in Dyker, G. *Angewandte Chimie Int'l Ed. in English*, Vol. 36, No. 16, 1700–2 (1997). The resulting N-substituted glycine may be converted to an N-substituted glyphosate by reacting it with formaldehyde and phosphorous acid ($H_3PO_3$) in the presence of a strong acid.

In a different embodiment of this invention, the N-substituted glycine is prepared by dehydrogenation of N-substituted ethanolamine in the presence of a base (preferably sodium hydroxide) to form salts of N-substituted glycines:

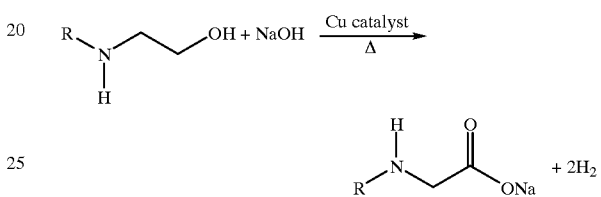

This reaction is described by Franczyk in U.S. Pat. Nos. 5,292,936 and 5,367,112, and by Ebner et al. in U.S. Pat. No. 5,627,125. The N-substituted ethanolamine precursor may be prepared in at least two ways. First, ketones may be condensed with monoethanolamine in the presence of hydrogen, a solvent, and a noble metal catalyst. This reaction is described in Cope, A. C. and Hancock, E. M. *J. Am. Chem. Soc.*, 64, 1503–6 (1942). N-substituted ethanolamines also may be prepared by reacting a mono-substituted amine (such as methylamine) with ethylene oxide to form the mono-substituted ethanolamine. This reaction is described by Y. Yoshida in Japanese Patent Application No. 95-141575. The resulting N-substituted glycine salt may be converted to N-substituted glyphosate by reacting it with phosphorus trichloride ($PCl_3$) in water, and then filtering out the salt and adding formaldehyde.

In an alternative embodiment of this invention, N-substituted glycine is prepared by condensation of N-substituted amides, formaldehyde, and carbon monoxide in the presence of a catalyst:

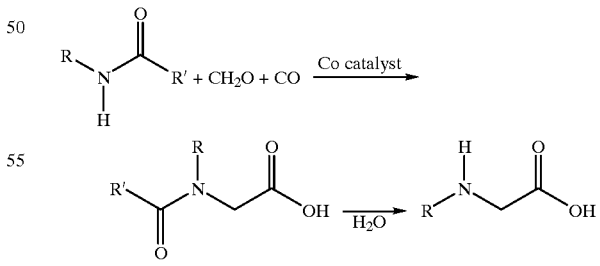

This reaction (i.e., carboxymethylation) is described by Beller et al. in European Patent Application No. 0680948; and Knifton, J. F. *Applied Homogeneous Catalysis* 159–68 (B. Cornils et al. eds., VCH, Weinheim, Germany 1996). The product of this reaction is the N-acetyl of the N-substituted glycine which may be hydrolyzed to the N-substituted glycine. The N-substituted glycine then may be converted into the corresponding N-substituted glyphosate by reacting it with phosphorous acid and formaldehyde in the presence of a strong acid, and then removing the carboxylic acid by methods generally known in the art, such as distillation or membrane separation.

In a further embodiment of this invention, the N-substituted glycine is prepared by the reductive alkylation of glycine achieved by reacting carbonyl compounds with glycine and hydrogen in the presence of a catalyst:

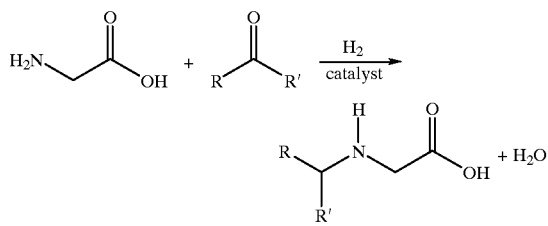

This reaction is described by Sartori et al. in U.S. Pat. No. 4,525,294. The N-substituted glycine may be converted to N-substituted glyphosate by reacting it with formaldehyde and phosphorous acid in the presence of a strong acid.

This invention also provides a new and useful method for conversion of N-substituted glyphosates which are not derived from the phosphonomethylation of N-substituted glycines. For example, this method is particularly useful for making glyphosate from NMG, an undesirable byproduct from the carbon-catalyzed oxidation of PMIDA.

FIG. 1 summarizes the methods for preparing glyphosate from the materials discussed above. The symbols used in FIG. 1 have the usual meanings familiar to those skilled in the art.

To oxidize the N-substituted glyphosate reactant, it preferably is first mixed with water and then fed into a reactor along with an oxygen-containing gas or a liquid containing dissolved oxygen. In the presence of a noble metal catalyst, the N-substituted glyphosate reactant is oxidatively converted into glyphosate and various byproducts:

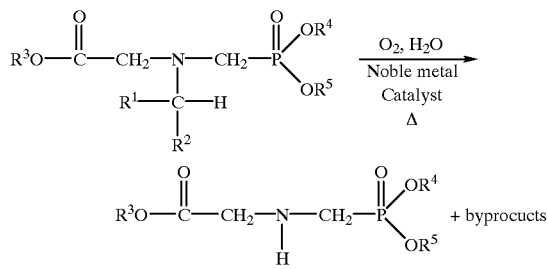

wherein $R^1$, $R^2$, $R^3$, $R^4$, and $R^5$ are defined as above. In a preferred embodiment, the catalyst subsequently is separated by filtration and the glyphosate then is isolated by precipitation, for example, by evaporation of a portion of the water and cooling.

The amount of N-substituted glyphosate reactant in the aqueous medium is typically from about 1 to about 80 wt. % ([mass of N-substituted glyphosate reactant÷total reaction mass]×100%). More preferably, the amount of N-substituted glyphosate reactant is from about 5 to about 50 wt. %, and most preferably from about 20 to about 40 wt. %.

Preferably, the reaction is conducted at a temperature of from about 50 to about 200° C. More preferably, the reaction is conducted at a temperature of from about 70 to about 150° C., and most preferably from about 125 to about 150° C.

The pressure in the reactor during the oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient to sustain the desired rate of reaction. The pressure preferably is at least equal to atmospheric pressure. Preferably, the pressure is from about 30 to 200 psig. More preferably, when the temperature is in the most preferred range of from about 125 to about 150° C., the pressure is from about 40 to about 100 psig.

The oxygen source for the oxidation reaction may be any oxygen-containing gas or a liquid containing dissolved oxygen. Preferably, the oxygen source is an oxygen-containing gas. As used herein, an "oxygen-containing gas" is any gaseous mixture containing molecular oxygen which optionally may contain one or more diluents which are non-reactive with the oxygen or the reactant or product under the reaction conditions. Examples of such gases are air, pure molecular oxygen, or molecular oxygen diluted with helium, argon, neon, nitrogen, or other non-molecular oxygen-containing gases. Preferably, at least about 20% by volume of the oxygen-containing gas is molecular oxygen, and more preferably, at least about 50% of the oxygen-containing gas is molecular oxygen.

The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the gas' contact with the reaction solution. Such contact may be obtained, for example, by dispersing the gas through a diffuser such as a porous glass frit or by sintering, shaking, or other methods known to those skilled in the art.

The oxygen preferably is fed to the reaction mixture at a rate which is sufficient to maintain the dissolved oxygen concentration at a finite level. More preferably, the oxygen is fed at a rate sufficient to maintain the dissolved oxygen concentration at no greater than about 2.0 ppm, but at a high enough concentration to sustain the desired reaction rate. It should be noted that the partial pressure of the oxygen in the reactor affects the rate at which oxygen is delivered to the reaction mixture and preferably is from about 0.5 to about 10 atm.

The catalyst used in this invention comprises a noble metal, preferably platinum (Pt), palladium (Pd), rhodium (Rh), iridium (Ir), osmium (Os), or gold (Au). In general, platinum and palladium are more preferred, and platinum is most preferred. Because platinum is presently most preferred, much of the following discussion will be directed to use of platinum. It should be understood, however, that the same discussion is generally applicable to the other noble metals and combinations thereof.

The noble metal catalyst may be unsupported, e.g., platinum black, commercially available from various sources such as Aldrich Chemical Co., Inc., Milwaukee, Wis.; Engelhard Corp., Iselin, N.J.; and Degussa Corp., Ridgefield Park, N.J. Alternatively, the noble metal catalyst may be deposited onto the surface of a support, such as carbon, alumina ($Al_2O_3$), silica ($SiO_2$), titania ($TiO_2$), zirconia ($ZrO_2$), siloxane, or barium sulfate ($BaSO_4$), preferably silica, titania, or barium sulfate. Supported metals are common in the art and may be commercially obtained from various sources, e.g., 5% platinum on activated carbon, Aldrich Catalogue No. 20,593-1; platinum on alumina powder, Aldrich Catalogue No. 31,132-4; palladium on barium sulfate (reduced), Aldrich Catalogue No. 27,799-1; and 5% Palladium on activated carbon, Aldrich Catalogue No. 20,568-0. As to carbon supports, graphitic supports generally are preferred because such supports tend to have greater glyphosate selectivity.

The concentration of the noble metal catalyst on a support's surface may vary within wide limits. Preferably it is in the range of from about 0.5 to about 20 wt. % ([mass of noble metal÷total mass of catalyst]×100%), more preferably from about 2.5 to about 10 wt. %, and most preferably from about 3 to about 7.5 wt. %. At concentrations greater than about 20 wt. %, layers and clumps of noble metal tend to form. Thus, there are fewer surface noble metal atoms per total amount of noble metal used. This tends to reduce the catalyst's activity and is an uneconomical use of the costly noble metal.

The weight ratio of the noble metal to the N-substituted glyphosate reactant in the reaction mixture preferably is from about 1:500 to about 1:5. More preferably, the ratio is from about 1:200 to about 1:10, and most preferably from about 1:50 to about 1:10.

In a preferred embodiment, a molecular electroactive species (i.e., a molecular species that may be reversibly oxidized or reduced by electron transfer) is adsorbed to the noble metal catalyst. It has been discovered in accordance with this invention that selectivity and/or conversion of the noble metal catalyst may be improved by the presence of the electroactive molecular species, particularly where the catalyst is being used to effect the oxidation of NMG to form glyphosate. In this instance, the electroactive molecular species preferably is hydrophobic and has an oxidation potential ($E_{1/2}$) of at least about 0.3 volts vs. SCE (saturated calomel electrode). Many such oxidation potentials may be found in the literature. A compilation showing the oxidation potential and reversibility for a large number of electroactive molecular species may be found in *Encyclopedia of Electrochemistry of the Elements* (A. Bard and H. Lund eds., Marcel Dekker, New York, publication dates vary between volumes). Specific references showing the oxidation potentials for electroactive molecular species are: for triphenylmethane, Perichon, J., Herlem, M., Bobilliart, F., and Thiebault, A. *Encyclopedia of Electrochemistry of the Elements* vol. 11, p. 163 (A. Bard and H. Lund eds., Marcel Dekker, New York, N.Y. 1978); for N-hydroxyphthalimide, Masui, M., Ueshima, T. Ozaki, S. *J.Chem. Soc. Chem. Commun.* 479–80 (1983); for tris(4-bromophenyl)amine, Dapperheld, S., Steckhan, E., Brinkhaus, K. *Chem. Ber.*, 124, 2557–67 (1991); for 2,2,6,6-tetramethyl piperidine N-oxide, Semmelhack, M., Chou, C., and Cortes, D. *J. Am. Chem. Soc.*, 105, 4492–4 (1983); for 5,10,15,20-tetrakis(pentafluorophenyl)-21H,23H-porphine iron (III) chloride, Dolphin, D., Traylor, T., and Xie, L. *Acc. Chem. Res.*, 30, 251–9 (1997); and for various porphyrins, Fuhrhop, J. H. *Porphyrins and Metalloporphyrins* 593 (K. Smith, ed., Elsevier, New York, 1975).

Electroactive molecular species also are useful in the context of the oxidation of N-isopropyl glyphosate to form glyphosate. In that context, an electroactive molecular species preferably is adsorbed to a noble metal catalyst on a graphitic carbon support. In the presence of the graphitic carbon support, the electroactive molecular species has been found to increase the noble metal catalyst's glyphosate selectivity.

Examples of generally suitable electroactive molecular species include triphenylmethane; N-hydroxyphthalimide; 5,10,15,20-tetrakis(pentafluorophenyl)-21H,23H-porphine iron (III) chloride (abbreviated "Fe(III)TPFPP chloride"); 2,4,7-trichlorofluorene; tris(4-bromophenyl)amine; 2,2,6,6-tetramethyl piperidine N-oxide (sometimes referred to as "TEMPO"); 5,10,15,20-tetraphenyl-21H,23H-porphine iron (III) chloride (sometimes referred to as "Fe(III)TPP chloride"); 4,4'-difluorobenzophenone; 5,10,15,20-tetraphenyl-21H,23H porphine nickel(II) (sometimes referred to as (Ni(II) TPP"); and phenothiazine. When the noble metal catalyst is being used to catalyze the oxidation of NMG to glyphosate, the most preferred electroactive molecular species include N-hydroxyphthalimide; tris(4-bromophenyl)amine; TEMPO; Fe(III)TPP chloride; and Ni(II) TPP.

Electroactive molecular species may be adsorbed to the noble metal catalyst using various methods generally known in the art. The electroactive molecular species may be added directly to the oxidation reaction mixture separately from the noble metal catalyst. For example, 2,2,6,6-tetramethyl piperidine N-oxide ("TEMPO") may be added to the reaction mixture without first being adsorbed to the noble metal catalyst, as illustrated in Example 13. Using this method, the electroactive molecular species adsorbs to the noble metal catalyst while in the reaction mixture. Alternatively, the electroactive molecular species is adsorbed to the noble metal catalyst before being added to the oxidation reaction mixture. Generally, the electroactive molecular species may be adsorbed to the catalyst using, for example, liquid phase deposition or gas phase deposition. Example 8 illustrates using liquid phase deposition to adsorb the electroactive molecular species.

The oxidation reaction preferably is carried out in a batch reactor so that the reaction may be contained until the conversion to glyphosate is complete. However, other types of reactors (e.g., continuous stirred tank reactors) also may be used, although preferably: (1) there should be sufficient contact between the oxygen, N-substituted glyphosate reactant, and the catalyst; and (2) there should be adequate retention time for substantial conversion of the N-substituted glyphosate reactant to glyphosate.

It should be noted that this invention has the ability to oxidize N-substituted glyphosates in the presence of other chemical species which may arise in the course of previously known methods for preparing glyphosate. For example, this invention has the ability to oxidize NMG in the presence of phosphoric acid or phosphonomethylated species which are byproducts of the carbon-catalyzed oxidation of PMIDA, such as aminomethylphosphonic acid ("AMPA"), N-methyl-aminomethylphosphonic acid ("MAMPA"), and glyphosate.

It should be further recognized that this reaction process may be conducted where a sub-stoichiometric amount (i.e., less than one equivalent) of base is present in the reaction mixture. The presence of the base, however, may be deleterious to selectivity under some reaction conditions.

EXAMPLES

General

Figure 2:
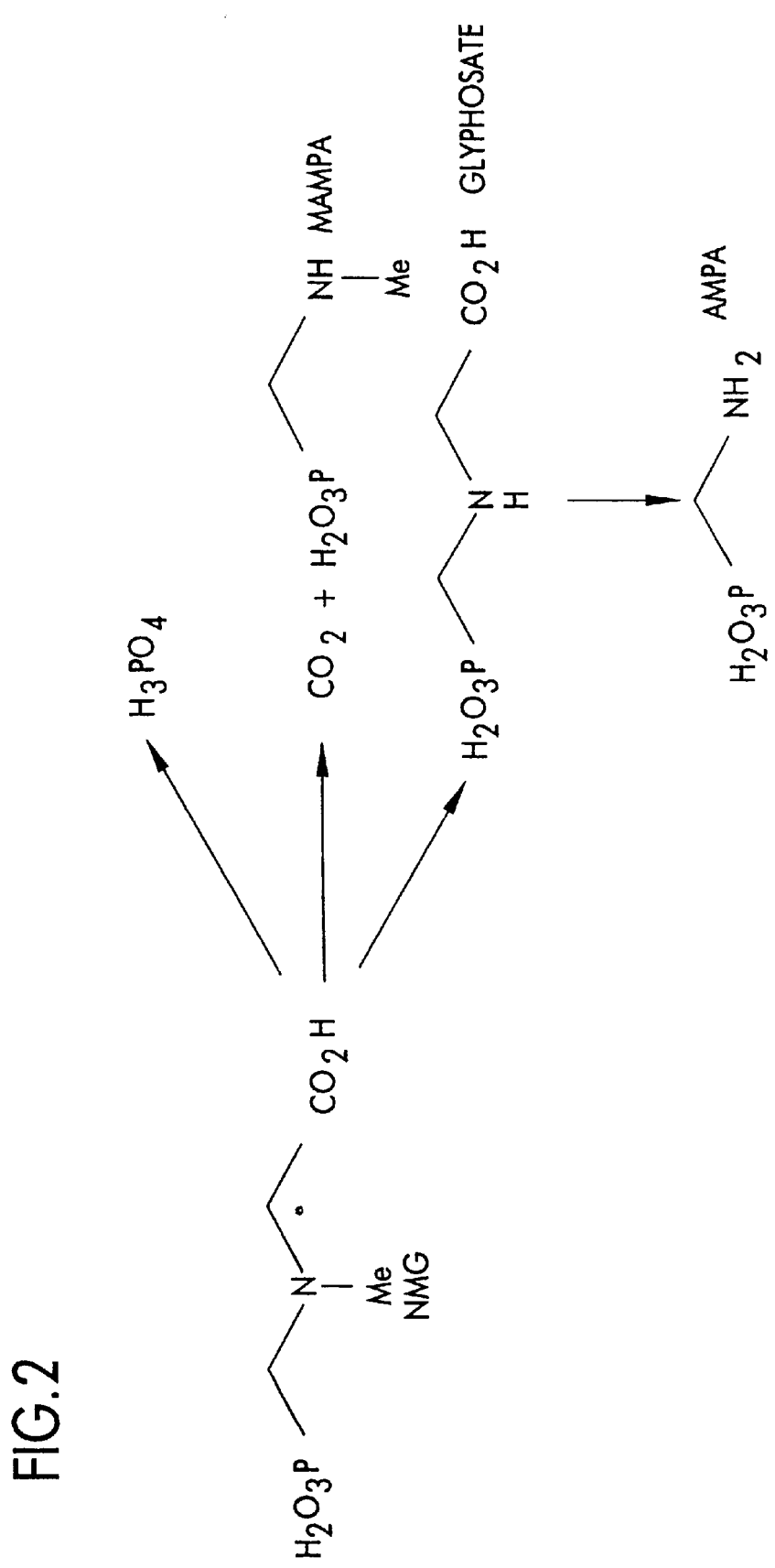
FIG. 2 summarizes various compounds that may be produced during the oxidation of NMG.

Most of the examples below describe the oxidation of NMG to form glyphosate. In addition to glyphosate, MAMPA and phosphoric acid ($H_3PO_4$) also may form. Further, the glyphosate product may further oxidize to form AMPA. This is summarized in FIG. 2.

High pressure liquid chromatography ("HPLC") was used to analyze the products formed during the reactions discussed in the following examples. An ion exchange separation was used, and the analytes were detected using UV/visible detection following post-column reaction to form a phosphomolybdate complex. This method can distinguish between, NMG, glyphosate, and phosphoric acid, but AMPA and MAMPA coelute. Because AMPA and MAMPA have the same response factor, on a molar basis, the sum of the AMPA and MAMPA concentrations can be reliably determined. This value is reported as (M)AMPA in the examples below.

Example 1

This example illustrates a typical synthesis of NMG. Approximately 89.9 g sarcosine (1.00 mole), 82.0 g phosphorous acid (1.0 mole), and 110 g concentrated hydrochloric acid were mixed and refluxed in a 130° C. oil bath. Next, 89.3 g of 37% formalin (1.1 mole) was added dropwise over 20 minutes and the reaction was continued for an additional 85 minutes. At this point, NMR revealed the following product distribution (on a molar basis): 89.9% NMG, 2.1% phosphorous acid, 1.9% phosphoric acid, 0.4% hydroxymethyl phosphorous acid, and 5.7% of an unknown product (NMR: triplet, 8.59 ppm). After cooling to room temperature, 40 g sodium hydroxide was added, followed by 250 g water. This led to the formation of a white precipitate which subsequently was recovered by filtration and assayed by HPLC. The total recovered yield of NMG was 70.5% based on the amount of sarcosine and phosphorous acid used.

Other N-alkyl glyphosates also may be made in a similar manner.

Example 2

This example illustrates the conversion of NMG to glyphosate using a Pt catalyst and oxygen.

Approximately 10.0 g NMG, 140 g water, and 1 g platinum black (Aldrich Chemical Co., Inc., Milwaukee, Wis.) were combined in a round bottom flask equipped with a water-cooled reflux condenser immersed in a 150° C. oil bath. Oxygen was bubbled through for four hours as the solution was stirred. At the end of this period, HPLC analysis revealed the following product distributions (on a molar basis): 86.4% glyphosate, 8.7% NMG, 2.2% (M)AMPA, and 2.7% phosphoric acid. Glyphosate precipitated from the solution after cooling to room temperature.

In a second experiment, a mixture of 10.0 g NMG, 2.0 g platinum black, and sufficient water to bring the total volume of the mixture to 200 ml, was stirred for 2 hours and 40 minutes at a temperature of 80° C. while oxygen at a pressure of one atmosphere was bubbled through. Analysis of the reaction mixture indicated the following product distribution in molar terms: 85.4% glyphosate, 8.1% phosphoric acid, and 6.5% unknown components. No NMG was detected.

Example 3

This example illustrates the conversion of N-isopropyl glyphosate to glyphosate using a Pt catalyst and oxygen. Approximately 1.0 g N-isopropyl glyphosate, 10 g water, and 0.3 g platinum black (Aldrich Chemical Co., Inc., Milwaukee, Wis.) were combined in a round bottom flask (equipped with a water-cooled reflux condenser) and immersed in a 80° C. oil bath. A stream of oxygen was introduced at the reaction surface for 18 hours as the solution was stirred. At the end of this period, $^{31}$P NMR revealed the following product distributions (on a molar basis): 91% glyphosate, 1% amino phosphonic acid, 6% phosphoric acid, and 2% unknown product (15.0 ppm). Glyphosate precipitated from solution after cooling to room temperature.

Example 4

Various N-alkyl glyphosates were used under the same conditions as described in Example 3 to produce glyphosate. In other words, the only parameter which was varied was R' in the following formula:

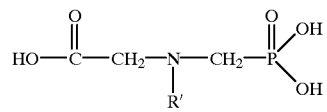

Table 1 shows the alkyl group (i.e., R') used, as well as the conversion and glyphosate selectivity.

TABLE 1

Use of Various N-Alkyl Glyphosates to Prepare Glyphosate

| Alkyl Group | Conversion (%) | Glyphosate Selectivity (%) |
| --- | --- | --- |
| methyl | 91 | 95 |
| isopropyl | 79 | 98 |
| isopropyl | 100 | 91 |
| n-pentyl | 62 | 82 |
| benzyl | 81 | 89 |
| cyclohexyl | 66 | 11 |

Example 5

This example illustrates the conversion of NMG to glyphosate using unsupported platinum and a variety of catalysts in which platinum is dispersed on a non-carbonaceous support.

Approximately 1.0 g NMG, 10 g water, and 2.0 g of 5% platinum on barium sulfate were combined in a round bottom flask (equipped with a water-cooled reflux condenser) and immersed in a 95° C. oil bath. Oxygen was bubbled through the reaction for 23 hours as the solution was stirred. At the end of this period, HPLC analysis revealed the following product distributions (on a molar basis): 78.2% glyphosate, 2.4% NMG, 9.4% (M)AMPA, and 10.0% phosphoric acid. Glyphosate precipitated from solution after cooling to room temperature.

In a separate experiment, the data in Table 2 was obtained by heating to reflux a mixture containing 1 g of NMG, 20 ml water, and sufficient catalyst to contain 5 mg of platinum metal in a magnetically-stirred, round-bottom flask equipped with a reflux condenser. Oxygen was bubbled through for 5 hours using a needle. The catalyst was then removed by filtration and the filtrate analyzed by HPLC.

As Table 2 indicates, two platinum black catalysts were tested. The Engelhard V2001 (Engelhard Corp., Iselin, N.J.) catalyst has a much smaller surface area than the Aldrich platinum black catalyst (Aldrich Chemical Co., Inc., Milwaukee, Wis.). As Table 2 shows, the Engelhard V2001 catalyst, with its lower surface area, had lower selectivity and conversion, even though 30 times more of the Engelhard catalyst (i.e., 150 mg) was used compared to the Aldrich catalyst (i.e., 5 mg).

TABLE 2

Use of Unsupported Pt and Pt Supported on a
Variety of Supports During NMG Oxidation

| Catalyst | Conversion (%) | Glyphosate Selectivity (%) | (M) AMPA Selectivity (%) | $H_3PO_4$ Selectivity (%) |
|---|---|---|---|---|
| Pt black (Aldrich) | 14.7 | 85.3 | 3.0 | 11.7 |
| Pt black (Engelhard V2001) (150 mg) | 2.7 | 70.0 | 17.9 | 12.1 |
| 5% Pt/$SnO_2$ | 18.0 | 88.7 | 2.6 | 8.7 |
| 5% Pt/$ZrO_2$ | 13.9 | 89.5 | 7.3 | 3.2 |
| 5% Pt/$BaSO_2$ | 31.2 | 92.2 | 2.8 | 5.1 |
| 5% Pt/$BaSO_4$ (different catalyst) | 34.0 | 88.6 | 2.8 | 8.7 |
| 5% Pt/$TiO_2$ | 47.4 | 91.9 | 1.7 | 6.4 |
| 5% Pt/$SiO_2$ | 23.7 | 88.9 | 2.3 | 8.8 |

A third experiment was conducted which illustrates that aluminum oxide and siloxanes (Deloxan, Degussa Corp., Ridgefield Park, N.J.) may be used as supports for the metal catalyst. The following experiments were conducted overnight at 95° C. and 1 atm using sufficient catalyst to be equivalent to 0.1 g platinum metal, 1 g NMG, and 10 ml of water. Oxygen was introduced through a needle at 50 sccm (i.e., standard $cm^3$ per min.) The resulting solution was filtered and analyzed by HPLC and the dissolved platinum concentration was analyzed by inductively-coupled plasma/mass spectrometry. The data is shown in Table 3.

TABLE 3

Use of Unsupported Pt and Pt Supported
on Various Supports During NMG Oxidation

| Catalyst | Conversion (%) | Glyphosate Selectivity (%) | (M) AMPA Selectivity (%) | $H_3PO_4$ Selectivity (%) |
|---|---|---|---|---|
| Pt black (Aldrich) | 98.5 | 85.7 | 6.1 | 8.2 |
| Pt black (Engelhard S3005) | 76 | 82.3 | 11.5 | 6.1 |
| 5% Pt/$SiO_2$ | 82.7 | 79.1 | 11.1 | 9.8 |
| 5% Pt/$SiO_2$ (different catalyst) | 96.7 | 83.6 | 10.6 | 5.9 |
| 5% Pt/$BaSO_4$ | 97.6 | 80.1 | 9.6 | 10.2 |
| 5% Pt/$TiO_2$ | 61.3 | 83.5 | 12.2 | 4.2 |
| 3% Pt/siloxane | 52.4 | 52.8 | 39.2 | 8.0 |
| 5% Pt/siloxane | 57.7 | 70.9 | 26.5 | 2.6 |
| 5% Pt/alumina | 33.8 | 46.7 | 44.4 | 8.9 |
| 5% Pt/alumina (different catalyst) | 48.5 | 37.9 | 50.1 | 5.8 |
| 5% Pt/alumina (different catalyst) | 55.2 | 44.4 | 51.6 | 4.0 |

Example 6

This example illustrates the use of palladium instead of platinum as a catalyst for the oxidation of NMG to glyphosate. A solution consisting of 3.0 g of NMG, 0.3 g of palladium black, and 57 g of water was refluxed in air over a weekend under a water-cooled reflux condenser. NMR analysis indicated the following product distribution: 97.2% NMG, 2.8% glyphosate, and 0.05% phosphoric acid.

Example 7

This example demonstrates that catalysts consisting of graphitic carbon supports impregnated with platinum have greater glyphosate selectivity relative to catalysts consisting of non-graphitic carbon supports impregnated with platinum. Also, this example demonstrates that less MAMPA and AMPA are formed when catalysts consisting of graphitic carbon supports impregnated with platinum are used.

The following example describes the results of oxidizing NMG using catalysts consisting of platinum dispersed on a commercially available carbon support. F106 carbon and the platinum/F106 carbon catalyst are available from Degussa Corp. (Ridgefield Park, N.J.). Sibunit carbon is manufactured as described in by Surovikin et al. in U.S. Pat. No. 4,978,649, and may be purchased from the Boreskov Institute of Catalysis in Novosibirsk, Russia as can platinum catalysts supported on Sibunit carbon. However, the catalyst used in this example was prepared from the carbon itself by impregnation with platinum salts followed by reduction with sodium borohydride which is a standard for the preparation of supported platinum catalysts. The general preparation of platinum on a carbon support is well-known in the art and is described, for example, in Stiles, A. B. *Catalyst Supports and Supported Catalysts, Theoretical and Applied Concepts* (Butterworths, Boston, Mass. 1987); and in a chapter by R. L. Moss in *Experimental Methods in Catalytic Research*, Vol. 2, Ch. 2, pp. 43–94 (R. B.Anderson & P. T. Dawson, eds., Academic Press, New York, N.Y. 1976). The 20% Pt/Vulcan XC-72R carbon catalyst is manufactured by Johnson-Matthey and may be purchased through Alfa/Aesar (Ward Hill, Mass.). These three carbons are respectively not graphitic, somewhat graphitic, and almost completely graphitic.

Approximately 100 mg of the catalyst (except as noted), 10 ml of water, and 1 g of NMG were refluxed for five hours while oxygen was bubbled through via a needle. The reaction was then filtered and analyzed by HPLC. Table 4 shows the results.

TABLE 4

Use of a Support Comprising Graphitic
Carbon During NMG Oxidation

| Catalyst | Conversion (%) | Glyphosate Selectivity (%) | (M) AMPA Selectivity (%) | $H_3PO_4$ Selectivity (%) |
|---|---|---|---|---|
| 5% Pt/F106 carbon ethanol-washed (50 mg) | 98.9 | 62.2 | 29.0 | 8.7 |
| 3% Pt/Sibunit carbon | 53.7 | 73.7 | 18.1 | 8.2 |
| 20% Pt/Vulcan XC-72R carbon | 53.6 | 83.5 | 10.4 | 6.1 |

Example 8

This example illustrates the improved selectivities which may be achieved when an electroactive molecular species is adsorbed to a noble metal catalyst. All of the electroactive molecular species adsorbed to platinum black in this example undergo oxidation and reduction by electron transfer. Thus, the treatment of platinum-containing catalysts by both electroactive molecular species and their oxidative precursors is exemplified herein.

This experiment was conducted by heating to reflux a mixture containing 1 g of NMG, 20 ml water, and 50 mg of platinum metal in a magnetically-stirred, round-bottom flask equipped with a reflux condenser. Oxygen was bubbled through for 5 hours using a needle. The catalyst was then removed by filtration and the filtrate analyzed by HPLC.

To prepare the organic-treated catalysts, 0.5 g of platinum black (Aldrich Chemical Co., Inc., Milwaukee, Wis.) was added to a solution of 25 mg of the poison (i.e., the electroactive molecular species) in 50 ml of anhydrous acetonitrile. The mixture sat capped in an Erlenmeyer flask for four days, except that the 4,4'-difluorobenzophenone catalyst only was exposed to solution for one day. The catalyst subsequently was recovered by filtration, rinsed with acetonitrile and diethyl ether, and air-dried overnight.

The 2,4,7-trichlorofluorene catalyst was prepared using 0.3 g of Pt black and 30 ml of a solution consisting of 834.5 ppm 2,4,7-trichlorofluorene in acetonitrile/1% $CH_2Cl_2$ solution (used to facilitate dissolution of the electroactive molecular species) which was allowed to evaporate at room temperature. The catalyst subsequently was washed with ethanol and air-dried.

The inorganic-treated catalysts were prepared by combining 0.50 g of Pt black, 50 ml of tetrahydrofuran, and either 25 or 100 mg of the inorganic electroactive molecular species, and stirring overnight at room temperature in a sealed 125 ml Erlenmeyer flask. The catalyst was recovered by filtration, washed with diethyl ether, and air-dried overnight.

The inorganic species used, all of which are available from Aldrich Chemical (Milwaukee, Wis.), were:
1. 5,10,15,20-tetrakis(pentafluorophenyl)-21H,23H-porphine iron (III) chloride (abbreviated "Fe(III)TPFPP chloride" in Table 5). Approximately 25 mg was used to prepare the catalyst.
2. 5,10,15,20-tetraphenyl-21H,23H-porphine iron (III) chloride (abbreviated "Fe(III) TPP chloride" in Table 5). Approximately 25 mg was used to prepare the catalyst.
3. 5,10,15,20-tetraphenyl-21H,23H-porphine nickel (II) (abbreviated as "Ni(II) TPP" in Table 5). Approximately 25 mg was used to prepare the catalyst.
4. Ruthenium-tris(2,2'-bipyridine) dichloride (abbreviated as "$[Ru(bby)_3Cl_2]$" in Table 5). Approximately 100 mg was used to prepare the catalyst.
5. Ferrocene. Approximately 100 mg was used to prepare the catalyst.

Where available, literature data on the oxidation potential ($E_{1/2}$) of the electroactive molecular species is reported in Table 5. This example illustrates that electroactive molecular species being relatively soluble in water (e.g., ferrocene and $[Ru(bpy)_3]Cl_2$) are less effective at enhancing glyphosate selectivity. This example also demonstrates that hydrophobic electroactive molecular species increase the catalyst's selectivity. Electroactive molecular species having oxidation potentials more negative than about +0.3 V vs SCE generally decrease conversion. Thus, the preferred electroactive molecular species for enhancing the selectivity and conversion of NMG oxidation may be either organic or inorganic, but should be hydrophobic and have oxidation potentials more positive than about 0.3 volts vs. SCE.

TABLE 5

Use of Electroactive Molecular Species on NMG Oxidation

| Poison | $E_{1/2}$ V vs SCE | Conv. (%) | Glyphosate Select (%) | MAMPA Select (%) | $H_3O_4$ Select (%) |
|---|---|---|---|---|---|
| None | — | 45.7 | 83.1 | 9.0 | 7.95 |
| 2,4,7-trichloro-fluorene | ? | 52.9 | 93.5 | 2.5 | 4.0 |
| N-hydroxy-phthalimide | +1.44 | 56.3 | 93.2 | 2.4 | 4.4 |

TABLE 5-continued

Use of Electroactive Molecular Species on NMG Oxidation

| Poison | $E_{1/2}$ V vs SCE | Conv. (%) | Glyphosate Select (%) | MAMPA Select (%) | $H_3O_4$ Select (%) |
|---|---|---|---|---|---|
| phthalimide tris(4-bromo-phenyl)amine | +1.05 | 35.3 | 93.5 | 2.5 | 4.0 |
| TEMPO | +0.6 | 71.2 | 92.9 | 2.4 | 4.6 |
| triphenyl-methane | +0.27 | 22.1 | 93.4 | ~0 | 6.6 |
| 4,4'-difluoro-benzophenone | ? | 8.6 | 91.4 | ~0 | 10.9 |
| Fe (III) TPFPP chloride | +0.07 | 22.9 | 89.7 | 4.0 | 6.3 |
| Fe (III) TPP chloride | +1.11 | 69.3 | 91.1 | 2.6 | 6.3 |
| Ni (II) TPP | +1.15 | 53.8 | 90.3 | 2.9 | 6.8 |
| $[Ru(bpy)_3]Cl_2$ | +1.32 | 37.9 | 68.9 | 12.1 | 19.1 |
| Ferrocene | +0.307 | 70.8 | 82.6 | 6.0 | 11.4 |

Example 9

This example illustrates the effect of electroactive molecular species on the platinum-catalyzed oxidation of N-isopropyl glyphosate using the commercially available catalyst 20% Pt on Vulcan XC-72R carbon (manufactured by Johnson-Matthey and is available from Alfa/Aesar (Ward Hill, Mass.)). The commercial catalyst was tested along with a catalyst which had been impregnated with two electroactive molecular species: N-hydroxyphthalimide and triphenylmethane.

These catalysts were used to oxidize N-isopropyl glyphosate by the method described in the previous example. Approximately 1 g of N-isopropyl glyphosate was substituted for the NMG. The results shown in Table 6 demonstrate that electroactive molecular species improve the selectivity of platinum on carbon catalysts for this reaction. Modifiers with less positive oxidation potentials such as triphenylmethane appear to be more effective than those with more positive oxidation potentials, such as N-hydroxyphthalimide. This example also demonstrates that the use of graphitic supports for platinum is less effective in suppressing undesired side reactions in N-isopropyl glyphosate oxidations than is the case for NMG.

TABLE 6

Use of Electroactive Molecular Species During Oxidation of N-Isopropyl Glyphosate

| Catalyst | $E_{1/2}$ V vs SCE | Conv. (%) | Glyphosate Select (%) | MAMPA Select (%) | $H_3O_4$ Select (%) |
|---|---|---|---|---|---|
| Platinum black | — | 77.0 | 79.8 | 8.9 | 11.3 |
| 20% Pt/Vulcan XC-72R carbon (25 mg used) | +0.07 | 81.9 | 20.5 | 72.1 | 7.4 |
| 20% Pt/Vulcan treated with N-hydroxy-phthalimide loading 35.3 mg/g (26 mg used) | +1.44 | 41.2 | 31.6 | 62.1 | 6.2 |

TABLE 6-continued

Use of Electroactive Molecular Species During Oxidation of N-Isopropyl Glyphosate

| Catalyst | $E_{1/2}$ V vs SCE | Conv. (%) | Glyphosate Select (%) | MAMPA Select (%) | $H_3O_4$ Select (%) |
|---|---|---|---|---|---|
| 20% Pt/Vulcan treated with triphenyl-methane loading 305 mg/g (32.6 mg used) | +0.27 | 60.2 | 50.1 | 25.4 | 24.5 |

Example 10

This example demonstrates that both selectivity and conversion may be improved by minimizing the dissolved oxygen concentration.

In a 300 mg 316 stainless steel autoclave reactor, 4.4 gram NMG were combined with 1 gram platinum black in 145 g deionized water. The reaction mixture was heated to 70° C. at 60 psig, and a nitrogen/oxygen mixture was bubbled through with vigorous mixing for 4 hours. The dissolved oxygen concentration was measured using an Orbisphere dissolved oxygen probe, calibrated to read 26.4 ppm $O_2$ at 70° C./60 psig air saturation, and controlled by varying the $N_2/O_2$ blend. Two runs were conducted with the dissolved $O_2$ concentration being maintained at 2–3 ppm and 10 ppm. HPLC analysis of the reaction mixture at 2 hrs and 4 hrs gave the results shown in Table 7.

TABLE 7

Minimizing Dissolved Oxygen Concentration During NMG Oxidation

| Dissolved Oxygen Concentration (ppm) | Time (hr) | Conv. (%) | Glyphosate Select (%) | MAMPA Select (%) | $H_3PO_4$ Select (%) |
|---|---|---|---|---|---|
| 2.75 | 2 | 66% | 75.96 | 5.48 | 18.56 |
| 2.75 | 4 | 82% | 76.16 | 5.95 | 17.89 |
| 10.4 | 2 | 60% | 70.70 | 14.97 | 14.33 |
| 10.2 | 4 | 76% | 69.83 | 16.21 | 13.97 |

Example 11

This example illustrates the platinum-catalyzed oxidation of N-substituted glyphosates in which the substituent on the nitrogen atom contains atoms other than carbon or hydrogen. In particular, it describes the oxidation of glyphosine ($-HO_2CCH_2N(CH_2PO_3H_2)_2$) and N-hydroxyethyl glyphosate, which are prepared by the phosphonomethylation of glycine and N-hydroxyethyl glycine respectively by reacting with formaldehyde and phosphorous acid in the presence of heat and a strong acid, as generally illustrated in Redmore, D. *Topics in Phosphorous Chemistry* Vol. 8, 15–85 (E. G. Griffith & M. Grayson eds., John Wiley & Sons 1976); and in a chapter entitled "α-substituted Phosphonates" in Mastalerz, P. *Handbook of Organophosphorus Chemistry* 277–375 (Robert Engel ed., Marcel Dekker 1992). Approximately 1 g of the substrate, 20 ml of water, and 50 mg of platinum black were combined in a round-bottom flask. The oxidation was conducted by the same procedure used for the oxidation of NMG in Example 8. The product distribution was analyzed via $^{31}P$ NMR. 74.9% of the glyphosine was oxidized with a glyphosate selectivity of 50.2%. The other major product was bis(phosphonomethyl) amine ($-HN(CH_2PO_3H_2)_2$) which accounted for 39.1% of the oxidized glyphosine. Small quantities of AMPA and of unidentified products also were detected. The use of the platinum black catalyst treated with tris(4-bromophenyl) amine described in Example 8 led to an increase in conversion to 86.8%, but no change in selectivity.

Oxidation of N-hydroxyethyl glyphosate resulted in 46.7% oxidation of the substrate and a product distribution of 61.2% glyphosate, 22.4% N-hydroxyethyl-aminomethylphosphonic acid, and 16.3% phosphoric acid.

Example 12

This example illustrates the rates and selectivities achievable by conducting the oxidation of NMG over platinum black at elevated temperature and the fact that no deactivation of the catalyst is detectable over seven cycles.

A 300 ml glass pressure bottle was equipped with a thermocouple and two fritted filters. One of the filters was located about half an inch above the center of the bottom of the bottle was used for gas dispersion. The second filter, located about an inch from the bottom and not centered, was used for the withdrawal of liquids. A gas exit line leading to a back pressure regulator was set to maintain the pressure at 50 psig also was provided. Approximately 60 g of NMG was loaded into the vessel along with 3 g of platinum black from Aldrich Chemical (Milwaukee, Wis.) and 180 ml of water, along with a stir bar. The bottle was immersed in an oil bath, magnetically stirred and heated under a slow nitrogen flow until the internal temperature reached 125° C., giving a homogeneous solution. Oxygen and nitrogen were then bubbled through the reaction mixture at rates of 1.5 and 0.5 slpm (i.e., standard liters per min.), respectively for 30 minutes followed by a further 30 minutes of reaction at a flow rate of 1 slpm each for oxygen and nitrogen, followed by a final 30 minutes with a nitrogen flow rate of 1.5 slpm and an oxygen flow rate of 0.5 slpm. Stirring was continued and the mixture remained homogeneous throughout the entire 90 minute period. A slow nitrogen flow was then established to maintain the pressure. The contents of the bottle were withdrawn through the liquid withdrawal frit, leaving the catalyst in the bottle. About 100 ml of water was injected through the frit and them withdrawn to remove residues from the reaction. The bottle was then allowed to cool. Again, 60 g of NMG and 180 ml of water was added and the cycle repeated. Seven such cycles were conducted with the results shown in Table 8.

Platinum concentrations in solution at the end of the run varied from 0.3 to 1.1 ppm after the first cycle as determined by inductively-coupled plasma mass spectrometry. Although a higher amount of platinum leached into solution during the first cycle (i.e., the concentration of dissolved platinum was 4.2 ppm), it is believed that most of the lost platinum was primarily unreduced platinum on the platinum black's surface.

TABLE 8

Repeated Oxidation of NMG over Pt Black at 125° C.

| Run no. | Conversion (%) | Glyphosate Selectivity (%) | (M) AMPA Selectivity (%) | $H_3PO_4$ Selectivity (%) |
|---|---|---|---|---|
| 1 | 89.8 | 82.4 | 5.6 | 12.0 |
| 2 | 80.9 | 87.1 | 3.6 | 9.2 |
| 3 | 84.7 | 79.0 | 8.5 | 12.5 |
| 4 | 66.7 | 83.4 | 5.6 | 11.0 |
| 5 | 79.1 | 81.8 | 7.6 | 10.6 |
| 6 | 75.6 | 79.5 | 7.3 | 13.2 |
| 7 | 78.1 | 79.4 | 9.0 | 11.6 |

Example 13

This example demonstrates the selectivities that may be achieved when N-alkyl glyphosates are oxidized at low rates of oxygen delivery and moderate conversion if an electroactive molecular species such as TEMPO (i.e., 2,2,6,6-tetramethyl piperidine N-oxide) is added to the reaction mixture. No pretreatment of the catalyst is required. This example further demonstrates that the conversion improves over the first few cycles when the electroactive molecular species is added to the mixture. Finally, this example demonstrates that the electroactive molecular species reduces the amount of noble metal loss.

Approximately 60 g of NMG, 180 ml of water, 3 g of platinum black (Aldrich Chemical, Milwaukee, Wis.), and 40 mg of TEMPO dissolved in 1 ml of acetonitrile were combined in the pressure reactor described in Example 12. The mixture was heated to 125° C. while stirring under a 50 psig nitrogen atmosphere, forming a homogeneous mixture. A nitrogen/oxygen mixture (75% nitrogen, 25% oxygen by volume) was bubbled through for 90 minutes at a flow rate of 1 slpm while the pressure was maintained at 50 psig. The reaction mixture then was withdrawn through a fritted filter, leaving the catalyst behind. Another 60 g of NMG, 180 ml of water, and 40 mg of TEMPO in 1 ml of acetonitrile subsequently was added to the flask and the cycle repeated. Four cycles in all were performed. In all cases, (M)AMPA concentrations were below the quantifiable limits, although traces were detected. The only quantifiable byproduct detected was phosphoric acid. The conversions and selectivities at the end of each of the four cycles are shown in Table 9.

As in Example 12, the concentration of dissolved platinum was determined at the end of each run by inductively-coupled plasma mass spectrometry. This dissolved platinum concentration was less than 0.1 ppm in cycles 2, 3, and 4. This is lower than the leaching observed in Example 12. As with Example 12, a higher amount of platinum leached into solution during the first cycle (i.e., the concentration of dissolved platinum was 8.3 ppm); however, it is believed that most of the lost platinum was primarily unreduced platinum on the platinum black's surface.

TABLE 9

Oxidation of NMG in the Presence of TEMPO at 125° C. for 90 Min.

| Cycle Number | Conversion (%) | Glyphosate Selectivity (%) | $H_3PO_4$ Selectivity (%) |
|---|---|---|---|
| 1 | 32.6 | 98.3 | 1.7 |
| 2 | 38.0 | 98.1 | 1.9 |
| 3 | 43.3 | 98.1 | 1.9 |
| 4 | 46.2 | 97.3 | 2.7 |

Example 14

These examples illustrate the selectivity achievable if NMG is prepared via the direct phosphonomethylation of sarcosine amides, such as N-acetyl and N-propionyl sarcosine or sarcosine anhydride rather than sarcosine itself.

Approximately 20.0 g N-acetyl sarcosine (152.5 mmole), 12.5 g phosphorous acid (152.4 mmole), and 37.6 g concentrated hydrochloric acid were mixed and refluxed in a 120° C. oil bath. Approximately 13.6 g of 37% formalin (167.6 mmol) was added dropwise over 20 minutes. The reaction was continued for an additional 19 hours. HPLC analysis revealed a 99% yield of NMG based on moles of charges.

Under the same conditions, 20.0 g N-propionylsarcosine (137.8 mmole) was converted into NMG using 11.3 g phosphorous acid (137.8 mmole), 10.0 g concentrated hydrochloric acid, and 12.3 g of 37% formalin (152.1 mmole). HPLC analysis revealed a 96.6% yield of NMG based on moles of N-propionylsarcosine charged.

Also under the same conditions, 2.06 g sarcosine anhydride (14.50 mmole) was converted into NMG using 2.38 g phosphorous acid (29.02 mmole), 5.7 g concentrated hydrochloric acid, and 2.6 g of 37% formalin (32.02 mmole). HPLC analysis revealed a 97.2% yield of NMG based on moles of sarcosine anhydride charged.

In an additional experiment, 2.0 g N-acetyl sarcosine (15.3 mmole) and 1.25 g phosphorous acid (15.3 mmole) were mixed with 3.1 g concentrated sulfuric acid and 1.7 g water and then refluxed in a 120° C. oil bath. Approximately 1.4 g of 37% formalin (16.7 mmol) was added dropwise over 20 minutes. The reaction was continued for an additional 18 hours. $^{31}P$ NMR analysis revealed a 98% yield of NMG based on moles of N-acetyl sarcosine charged.

Example 15

This example demonstrates oxidizing NMG under conditions very similar to those of Example 12, except that a sub-stoichiometric base is present in the reaction mixture.

Approximately 60 g NMG, 9.6 g of 28–30% ammonium hydroxide (0.25 equivalents), and 170 ml water were combined in the apparatus described in Example 12 and stirred for one hour at an internal temperature of 125° C. while 0.75 slpm of pure oxygen was bubbled through at a pressure of 50 psig. HPLC analysis of the reaction mixture indicated that 23.5% of the NMG had been oxidized with a selectivity to glyphosate of 65.7%. The selectivities of (M)AMPA and $H_3PO_4$ were 21.1% and 13.2%, respectively.

As the results indicate, the NMG oxidation proceeds, although conversion and selectivity were lower compared to a reaction conducted in the absence of base.

Example 16

This example demonstrates that NMG may be oxidized selectively to glyphosate in the presence of glyphosate and similar compounds. One gram of platinum black was combined with 300 g of a solution containing about 6% NMG and lesser quantities of glyphosate, AMPA, MAMPA, formaldehyde, formic acid, and sodium chloride. The mixture was heated to 150° C. for 4 hours while oxygen was passed through the reactor at a pressure of 70 psig. At the conclusion of the reaction, NMR and HPLC analysis indicated that most of the NMG had been converted to glyphosate.

The above description of the preferred embodiment is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments and may be variously modified.

We claim:

1. A process for the preparation of glyphosate, a salt of glyphosate, or an ester of glyphosate, the process comprising contacting a solution containing an N-substituted glyphosate with oxygen in the presence of a noble metal catalyst to increase the amount of said glypliosate, salt, or ester in the solution, wherein the N-substituted glyphosate has the formula (II):

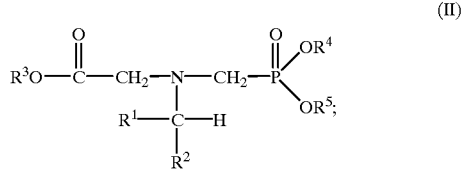

$R^1$ and $R^2$ are independently hydrogen, halogen, —$PO_3H_2$, $SO_3H$, —$NO_2$, hydrocarbyl, or substituted hydrocarbyl, except that neither $R^1$ nor $R^2$ is —$CO_2H$; and $R^3$, $R^4$, and $R^5$ are independently hydrogen, hydrocarbyl, substituted hydrocarbyl, or an agronomically acceptable cation.

2. The process recited in claim 1 wherein $R^3$, $R^4$, and $R^5$ are independently hydrogen or an agronomically acceptable cation.

3. The process recited in claim 2 wherein $R^1$ is hydrogen and $R^2$ is —$PO_3H_2$.

4. The process recited in claim 2 wherein $R^1$ is hydrogen and $R^2$ is a linear, branched, or cyclic hydrocarbyl containing up to about 19 carbon atoms.

5. The process recited in claim 2 wherein $R^1$ and $R^2$ are hydrogen.

6. The process recited in claim 5 wherein the noble metal catalyst is on a support surface, the support comprising graphitic carbon.

7. The process recited in claim 5 wherein the noble metal catalyst has a hydrophobic electroactive molecular species adsorbed thereon.

8. The process recited in claim 7 wherein the electroactive molecular species has an oxidation potential of at least about 0.3 volts vs. SCE.

9. The process recited in claim 7 wherein the electroactive molecular species is triphenylmethane; N-hydroxyphthalimide; 2,4,7-trichlorofluorene; tris(4-bromophenyl)amine; 2,2,6,6-tetramethyl piperidine N-oxide; 5,10,15,20-tetraphenyl-21H,23H-porphine iron (III) chloride; 5,10,15,20-tetraphenyl-21H,23H porphine nickel(II); 4,4'-difluorobenzophenone; 5,10,15,20-tetrakis (pentafluorophenyl)-21H,23H-porphine iron (III) chloride; or phenothiazine.

10. The process recited in claim 7 wherein the electroactive molecular species is N-hydroxyphthalimide; tris(4-bromophenyl)amine; 2,2,6,6-tetramethyl piperidine N-oxide; 5,10,15,20-tetraphenyl-21H,23H-porphine iron (III) chloride; 5,10,15,20-tetraphenyl-21H,23H porphine nickel(II); or phenothiazine.

11. The process recited in claim 7 wherein the electroactive molecular species is N-hydroxyphthalimide; 2,2,6,6-tetramethyl piperidine N-oxide; 5,10,15,20-tetraphenyl-21H,23H-porphine iron(III) chloride; or 5,10,15,20-tetraphenyl-21H,23H porphine nickel(II).

12. The process recited in claim 7 wherein the electroactive molecular species is 2,2,6,6-tetramethyl piperidine N-oxide.

13. The process recited in claim 7 wherein the electroactive molecular species is phenothiazine.

14. The process recited in claim 7 wherein the noble metal catalyst comprises platinum.

15. The process recited in claim 5 wherein the solution further contains a phosphonomethylated species in addition to the N-substituted glyphosate.

16. The process recited in claim 5 wherein the solution further contains glyphosate, aminomethylphosphonic acid, N-methyl-aminomethylphosphonic acid, or phosphoric acid.

17. The process recited in claim 2 wherein $R^1$ and $R^2$ are —$CH_3$.

18. The process recited in claim 17 wherein: (a) the noble metal catalyst is on a support surface, the support comprising graphitic carbon; and (b) the noble metal catalyst has a hydrophobic electroactive molecular species adsorbed thereon.

19. The process recited in claim 18 wherein the electroactive molecular species is triphenylmethane; N-hydroxyphthalimide; 2,4,7-trichlorofluorene; tris(4-bromophenyl)amine; 2,2,6,6-tetramethyl piperidine N-oxide; 5,10,15,20-tetraphenyl-21H,23H-porphine iron (III) chloride; 5,10,15,20-tetraphenyl-21H,23H porphine nickel(II); 4,4'-difluorobenzophenone; 5,10,15,20-tetrakis (pentafluorophenyl)-21H,23H-porphine iron (III) chloride; or phenothiazine.

20. The process recited in claim 18 wherein the electroactive molecular species is triphenylmethane or N-hydroxyphthalimide.

21. The process recited in claim 2 wherein $R^1$ is hydrogen and $R^2$ is a straight-chain hydrocarbyl containing 4 carbon atoms.

22. The process recited in claim 2 wherein $R^1$ is hydrogen and $R^2$ is phenyl.

23. The process recited in claim 1 wherein the noble metal catalyst comprises palladium or platinum.

24. The process recited in claim 1 wherein the noble metal catalyst comprises platinum.

25. The process recited in claim 1 wherein the noble metal catalyst is on a support surface, the support comprising carbon, alumina, silica, titania, zirconia, siloxane, or barium sulfate.

26. The process recited in claim 25 wherein the support comprises silica, titania, and barium sulfate.

27. The process recited in claim 25 wherein the support comprises graphitic carbon.

28. The process recited in claim 27 wherein the noble metal catalyst comprises platinum.

29. The process recited in claim 1 wherein the oxygen is fed at a rate which imparts a finite dissolved oxygen concentration in the solution that is no greater than 2.0 ppm.

30. The process recited in claim 1 wherein the weight ratio of the noble metal catalyst to the N-substituted glyphosate is from about 1:500 to about 1:5.

31. The process recited in claim 1 wherein weight ratio of the noble metal catalyst to the N-substituted glyphosate is from about 1:200 to about 1:10.

32. The process recited in claim 1 wherein weight ratio of the noble metal catalyst to the N-substituted glyphosate is from about 1:50 to about 1:10.

33. The process recited in claim 1 wherein the process is operated at a temperature of from about 50 to about 200° C.

34. The process recited in claim 1 wherein the process is operated at a temperature of from about 70 to about 150° C.

35. The process recited in claim 1 wherein the process is operated at a temperature of from about 125 to about 150° C.

36. The process recited in claim 1 wherein the process is operated at a temperature of from about 125 to about 150° C. and at a pressure of from about 40 psig to about 100 psig.

37. The process recited in claim 1 wherein the process is operated under a gaseous environment having an oxygen partial pressure of from about 0.5 to about 10 atm.

38. The process recited in claim 1 further comprising adding 2,2,6,6-tetramethyl piperidine N-oxide to the solution.

39. The process recited in claim 1 further comprising adding a sub-stoichiometric amount of base to the solution.

40. The process recited in claim 1 wherein the solution further contains a phosphonomethylated species in addition to the N-substituted glyphosate.

41. The process recited in claim 1 wherein the solution arises from the oxidation of N-(phosphonomethyl) iminodiacetic acid.

42. The process recited in claim 1 wherein the solution further contains glyphosate, aminomethylphosphonic acid, N-methyl-aminomethylphosphonic acid, or phosphoric acid.

43. A process for the preparation of glyphosate, or a salt of glyphosate, the process comprising contacting a solution containing an N-substituted glyphosate with a catalyst comprising platinum, introducing 2,2,6,6-tetramethyl piperidine N-oxide into the solution, and introducing oxygen into the solution at a rate which imparts a finite dissolved oxygen concentration in the solution that is no greater than 2.0 ppm, wherein the solution has a temperature of from about 125 to about 150° C.;

the N-substituted glyphosate has the formula (II):

$$R^3O-\overset{O}{\underset{}{C}}-CH_2-\underset{\underset{R^2}{\overset{|}{C}-H}}{\overset{|}{N}}-CH_2-\overset{O}{\underset{}{P}}\overset{OR^4}{\underset{OR^5}{}};$$ (II)

$R^1$ and $R^2$ are hydrogen; and $R^3$, $R^4$, and $R^5$ are independently hydrogen or an agronomically acceptable cation.

44. The process recited in claim 1 wherein the noble metal catalyst comprises platinum, palladium, rhodium, iridium, osmium, or gold.

45. The process recited in claim 1 wherein from about 0.11 to about 0.98 moles of said glyphosate, salt, or ester are formed per mole of N-substituted glyphosate consumed.

46. The process recited in claim 1 wherein from about 0.20 to about 0.98 moles of said glyphosate, salt, or ester are formed per mole of N-substituted glyphosate consumed.

47. The process recited in claim 1 wherein from about 0.32 to about 0.98 moles of said glyphosate, salt, or ester are formed per mole of N-substituted glyphosate consumed.

48. The process recited in claim 1 wherein from about 0.50 to about 0.98 moles of said glyphosate, salt, or ester are formed per mole of N-substituted glyphosate consumed.

49. The process recited in claim 1 wherein from about 0.70 to about 0.98 moles of said glyphosate, salt, or ester are formed per mole of N-substituted glyphosate consumed.

50. The process recited in claim 1 wherein from about 0.80 to about 0.98 moles of said glyphosate, salt, or ester are formed per mole of N-substituted glyphosato consumed.

* * * * *

UNITED STATES PATENT AND TRADEMARK OFFICE
CERTIFICATE OF CORRECTION

PATENT NO.    : 6,005,140
DATED         : December 21, 1999
INVENTOR(S)   : David A. Morgenstern et al.

It is certified that error appears in the above-identified patent and that said Letters Patent is hereby corrected as shown below:

Title page,
Amendment A Before Examination was not entered. Please enter the following immediately after the title on the first page -- This patent claims priority from PCT Application No. U.S. 98/002,883 filed on February 12, 1998 --.

Column 15,
Line 60, "$H_3O_4$" should read -- $H_3PO_4$ --.

Column 16,
Line 55, "$H_3O_4$" should read -- $H_3PO_4$ --.

Column 21, claim 1,
Line 23, "glypliosate" should read -- glyphosate --.

Column 24, claim 50,
Line 39, "glyphosato" should read -- glyphosate --.

Signed and Sealed this

Eighth Day of January, 2002

Attest:

JAMES E. ROGAN
Attesting Officer    Director of the United States Patent and Trademark Office